United States Patent [19]
Evans et al.

[11] Patent Number: 5,980,548
[45] Date of Patent: Nov. 9, 1999

[54] TRANSMYOCARDIAL REVASCULARIZATION SYSTEM

[75] Inventors: Douglas G. Evans; John E. Nash, both of Downington, Pa.

[73] Assignee: Kensey Nash Corporation, Exton, Pa.

[21] Appl. No.: 08/958,788

[22] Filed: Oct. 29, 1997

[51] Int. Cl.$^6$ .................................................. A61B 17/34
[52] U.S. Cl. ................................... 606/185; 606/220
[58] Field of Search ............................ 606/185, 186, 606/213, 219, 220

[56] References Cited

U.S. PATENT DOCUMENTS

| | | |
|---|---|---|
| 4,658,817 | 4/1987 | Hardy . |
| 4,669,473 | 6/1987 | Richards et al. .......................... 606/220 |
| 5,287,861 | 2/1994 | Wilk .......................................... 128/898 |
| 5,500,000 | 3/1996 | Feagin et al. ............................. 606/220 |
| 5,591,159 | 1/1997 | Taheri . |
| 5,607,421 | 3/1997 | Jeevanandam et al. . |
| 5,655,548 | 8/1997 | Nelson et al. . |
| 5,728,114 | 3/1998 | Evans et al. ............................. 606/213 |

FOREIGN PATENT DOCUMENTS

| | | |
|---|---|---|
| 0 876 803 A2 | of 0000 | European Pat. Off. . |
| 196 45 183 A1 | of 0000 | Germany . |
| 296 19 029 | 4/1997 | Germany ........................ A61B 17/34 |
| WO 97/32551 | 9/1997 | WIPO . |

OTHER PUBLICATIONS

New Concepts in Revascularization of Myocardium by Mirhoseini et al. In Ann. Thor. Surg., 45:415–420, Apr., 1998.

Myocardial Revascularization by a New Method of Carrying Blood Directly From the Left Ventricular Cavity Into the Coronary Circulation by Massimo et al. appearing in J. Thorac. Surg., 34:257–264, Aug., 1957.

Experimental Method for Producing a Collageral Circulation to the Heart Directly From the Left Ventricle by Goldman et al. in the Journal of Thoracic and Cardiovascular Surgery, 31:364–374, Mar., 1965.

Transmyocardial Acupunture: A New Approach to Myocardial Revascularization by Sen et al. in the Journal of Thoracic and Cardiovascular Surgery, 50:181–187, Aug., 1965.

Transmyocardial Laser Revascularization–Morphologic Pathophysiologic and Historical Principles of Indirect Revascularization of the Heart Muscle in Z Kardiol, 86(3): 147–164, Mar., 1997.

Histological Findings After Transmyocardial Laser Revascularization by Krabatsch et al. appearing in J. Card. Surg. 11:326–331, 1996.

Transmyocardial Laser Revascularization. Historical Features in Human Nonresponder Myocardium appearing in Circulation, 95(c): 371–375, Jan. 21, 1997.

*Primary Examiner*—Michael Buiz
*Assistant Examiner*—Kevin Truong
*Attorney, Agent, or Firm*—Caesar, Rivise, Bernstein, Cohen & Pokotilow, Ltd.

[57] ABSTRACT

A transmyocardial revascularization system including a plurality of inserts formed of a material to elicit a healing response in tissue of the myocardium and deployment instruments and associated components for deploying the inserts into the wall of the myocardium. The inserts are arranged to be disposed within respective lumens or channels in the wall of the myocardium. The inserts can take various forms, e.g., be solid members, tubular members, or porous members, and may be resorbable, partially resorbable or nonresorbable. In some embodiments the inserts are arranged to be left in place within the channels in the wall of the myocardium to result in plural lumens which enable blood to flow therethrough and into contiguous capillaries. The deployment instruments are arranged to pierce the tissue of the myocardium from either the endocardium or the epicardium to insert the inserts into the myocardium, depending on the particular deployment instrument used. The deployment instruments may make use of a stabilizing device to stabilize them during the procedure of inserting the inserts into the myocardium. A controller may also be provided as part of the system to coordinate the operation of the deployment instrument with the cardiac cycle. The formation of the lumens can be achieved either by the inserts or by some other means, such as a piercing tip or an energy applicator forming a portion of the instrument. The inserts may include one or more of pharmaceuticals, biologically active agents, radiopaque materials, etc.

42 Claims, 10 Drawing Sheets

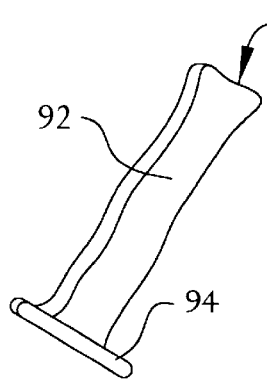
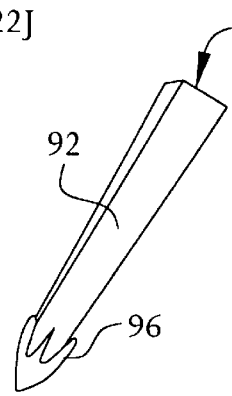
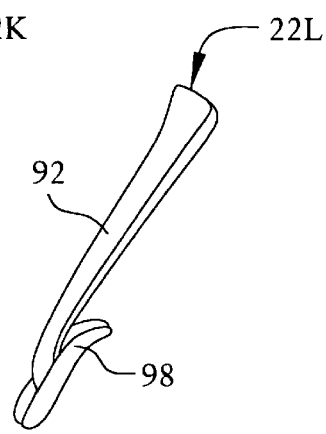
FIG. 9J   FIG. 9K   FIG. 9L
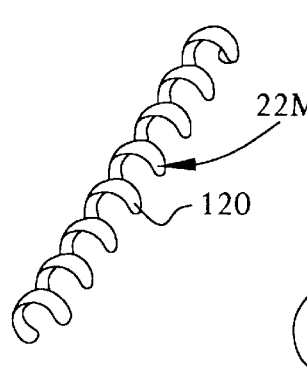
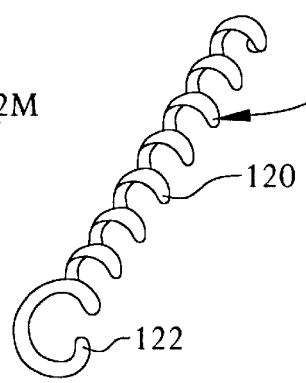
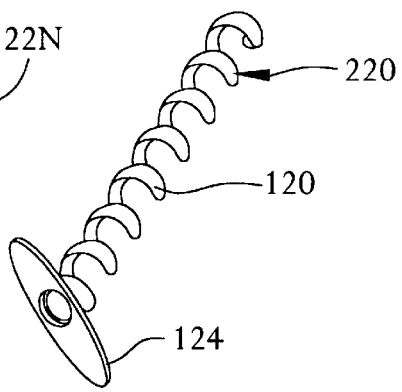
FIG. 9M   FIG. 9N   FIG. 9O
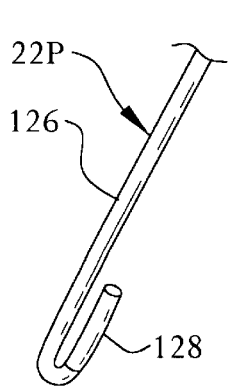
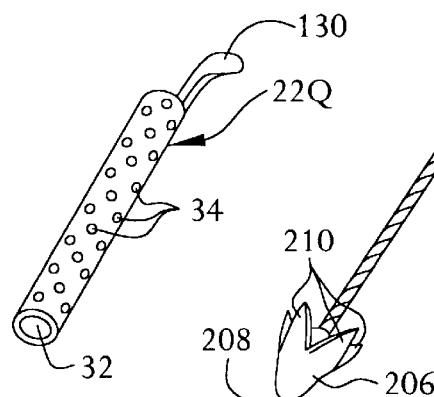
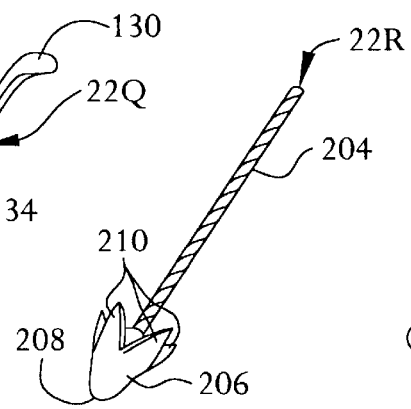
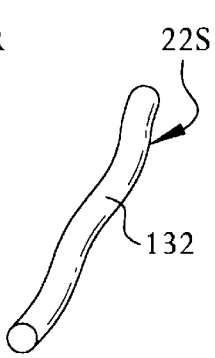
FIG. 9P   FIG. 9Q   FIG. 9R   FIG. 9S 5,980,548

TRANSMYOCARDIAL REVASCULARIZATION SYSTEM

BACKGROUND OF THE INVENTION

This invention relates generally to medical systems and procedures and more particularly to systems and procedures for effecting revascularization of the myocardium of a living being.

Atherosclerosis is the leading causes of death in the industrial world today. During the disease process, atherosclerotic plaques develop at various locations within the arterial system of those affected. These plaques restrict the flow of blood through the affected vessels. Of particular concern is when these plaques develop within the blood vessels that feed the muscles of the heart. In healthy hearts, cardiac blood perfusion results from the two coronary arterial vessels, the left and right coronary arteries which perfuse the myocardium from the epicardial surface inward towards the endocardium. The blood flows through the capillary system into the coronary veins and into the right atrium via the coronary sinus. When atherosclerosis occurs within the arteries of the heart it leads to myocardial infarctions, or heart attacks, and ischemia due to reduced blood flow to the heart muscle.

Over the past few years numerous methods for treating cardiovascular disease have become available. Traditional methods utilize open surgical procedures to access the heart and bypass blockages in the coronary blood vessels. In these procedures, the patient's heart is surgically exposed and one or more coronary arteries are replaced/bypassed with synthetic or natural bypass grafts. During conventional cardiac surgery, the heart is stopped using cardioplegia solutions and the patient is put on cardiopulmonary bypass which uses a heart-lung machine to maintain circulation throughout the body during the surgical procedure. A state of hypothermia is induced in the heart tissue during the bypass procedure to preserve the tissue from necrosis. Once the procedure is complete, the heart is resuscitated and the patient is removed from bypass. There are great risks associated with these surgical procedures such as significant pain, extended rehabilitation times, and high risk of mortality for the patient. The procedure is time-consuming and costly to perform. This surgery also requires that the patient have both adequate lung and kidney function in order to tolerate the circulatory bypass associated with the procedure and a number of patients which are medically unstable are thus not a candidate for bypass surgery. As a result, over the past few years minimally invasive techniques for performing bypass surgery have been developed and in some instances the need for cardiopulmonary bypass and extended recovery times are avoided. In addition, as an alternative to surgical methods, non-surgical procedures, such as percutaneous transluminal coronary angioplasty, rotational atherectomy, and stenting have been successfully used to treat this disease in a less invasive non-surgical fashion.

In balloon angioplasty a long, thin catheter containing a tiny inflatable balloon at its distal end is threaded through the cardiovascular system until the balloon is located at the location of the narrowed blood vessel. The balloon is then inflated to compress the obstructing plaque against the arterial wall, thereby restoring or improving the flow of blood to the local and distal tissues. Rotational atherectomy utilizes a similarly long and thin catheter, but with a rotational cutting tip at its distal end for cutting through the occluding material. Stenting utilizes a balloon tipped catheter to expand a small coil-spring-like scaffold at the site of the blockage to hold the blood vessel open. While many patients are successfully relieved of their symptoms and pain, in a significant number of patients, the blood vessels eventually reocclude within a relatively short period of time. In addition, for a large number of patients that are in the later stages of ischemic heart disease, the current technology offers little hope for long term cure. In these patients even extending the patient's life for several months provides a significant benefit to the patients and their families.

Although these non-surgical procedures are much less costly and less traumatic to the patient than coronary bypass surgery there are a number of patients for which these procedures are not suitable. For certain types of patients the presence of extremely diffuse stenotic lesions and total occlusion in tortuous vessels prohibits them from being candidates. In addition to these procedures which attempt to reopen or bypass the coronary vessels, direct myocardial revascularization has been performed by inducing the creation of new channels, other than the coronary arteries themselves, to supply oxygenated blood and remove waste products from the heart tissue. Myocardial revascularization is a technique used to supplement the blood supply delivered to the heart by providing the ischemic inner surface of the heart, known as the endocardium, with direct access to the blood within the ventricular chamber. Typically the endocardium receives its nutrient blood supply entirely from the coronary arteries that branch through the heart wall from the outer surface known as the epicardium.

In an article entitled "New Concepts In Revascularization Of Myocardium" by Mirhoseini et al. in Ann. Thor. Surg., 45:415–420, April, 1988 the work of investigators exploring several different approaches for direct revascularization of ischemic myocardium is discussed. One revascularization technique utilizes "myoepexy", which consists of roughening of the myocardial surface to enhance capillarization. Another technique, known as "omentopexy", consists of sewing the omentum over the heart to provide a new blood supply. Another approach involves implanting the left internal mammary artery directly into heart muscle so that blood flowing through the side branches of the artery will perfuse the muscle.

Similar revascularization techniques have involved the use of polyethylene tubes, endocardial incisions, and the creation of perforated or bored channels with various types of needles, and needle acupuncture. For example, T-shaped tubes have been implanted in the muscle, with the leg of the T-tube extending into the ventricular cavity as reported by Massimo et al. in an article entitled "Myocardial Revascularization By A New Method Of Carrying Blood Directly From The Left Ventricular Cavity Into The Coronary Circulation" appearing in J. Thorac. Surg., 34:257–264, August, 1957. In an article entitled "Experimental Method For Producing A Collageral Circulation To The Heart Directly From The Left Ventricle" by Goldman et al. in the Journal of Thoracic and Cardiovascular Surgery, 31:364–374, March, 1965, several experimental methods for myocardial revascularization are described. One method involved the implantation of excised perforated carotid arteries into the left ventricular wall. Goldman et al. also examined the use of implanted perforated polyethylene tubing in a similar fashion.

Needle acupuncture approaches to direct myocardial revascularization have been made and were based upon the premise that the heart of reptiles achieve myocardial perfusion via small channels between the left ventricle and the coronary arterial tree as described by Sen et al. in their article entitled "Transmyocardial Acupuncture: A New Approach To Myocardial Revascularization" in the Journal of Thoracic and Cardiovascular Surgery, 50:181–187, August, 1965. In that article it was reported that researchers attempted to duplicate the reptilian anatomy to provide for better perfusion in human myocardium by perforating portions of the ventricular myocardium with 1.2 mm diameter needles in 20 locations per square centimeter. It has been shown that the perfusion channels formed by mechanical methods such as acupuncture generally close within two or three months due to fibrosis and scaring. As a result these types of mechanical approaches have been abandoned in favor of the use of lasers to effect the transmyocardial revascularization (TMR).

U.S. Pat. No. 5,591,159 (Taheri) describes a device for effecting myocardial perfusion that utilizes slit needles to perforate the myocardium. The needles may also utilize a laser beam directed through the lumens of the needles. The device uses a trans-femoral approach to position the device into the left ventricle of the patient. A plunger is activated to cause the needles to enter the myocardium several times. Perforation of the myocardium may be effected by means of a laser beam through the lumen of the needle or high velocity drill.

U.S. Pat. No. 5,655,548 (Nelson et al.) describes a method for perfusing the myocardium using a conduit disposed between the left ventricle and the coronary sinus. In one method, an opening is formed between the left ventricle and the coronary sinus, and the coronary ostium is partially occluded using a stent that prevents the pressure in the coronary sinus from exceeding a predetermined value. Blood ejected from the left ventricle enters the coronary sinus during cardiac systole. The apparatus limits the peak pressure in the coronary sinus to minimize edema of the venous system. The system utilizes retroperfusion via the coronary sinus of the venous system.

Previous researchers had explored long term retroperfusion via the coronary sinus but found that its leads to edema of the cardiac veins which are incapable of sustaining long-term pressures above about 60 mm Hg. The procedure basically places a stent-like plug in the left ventricle so that blood flows into the coronary sinus and then into the myocardium via the venous system using retroperfusion, not into the myocardium directly. In the aforementioned Nelson et al. patent there is disclosed the use of a cutting instrument, such as a cannulated needle, a rotating blade, or medical laser to provide the required opening for the conduit. It is believed that when implanted in the heart, the plug and stent will result in long-term retrograde perfusion of the myocardium using the cardiac venous system and will cause a redistribution of the flow within the venous system so that a greater fraction of the deoxygenated blood will exit through the lymphatic stem and the Thebesian veins. The inventors also describe the use of a conduit which takes the place of the coronary sinus.

U.S. Pat. No. 4,658,817 (Hardy) describes a surgical carbon dioxide laser with a hollow needle mounted on the forward end of the handpiece. The needle is used to perforate a portion of the tissue, for instance the epicardium, to provide the laser beam direct access to distal tissue of the endocardium for lasering and vaporization. The device does not vaporize the tissue of the outer wall instead it separates the tissue which recoils to its native position after the needle's removal. This technique eliminates surface bleeding and the need for suturing the epicardium as is done with other techniques.

In U.S. Pat. No. 5,607,421 (Jeevanandam) discloses that laser channels remain open because carbonization associated with the laser energy inhibits lymphocyte, macrophage, and fibroblast migration. Thus, in contrast to channels created by needle acupuncture, laser channels heal more slowly and with less scar formation which allows endothelialization and long term patency.

It has been reported by Moosdorf et al. in their article entitled "Transmyocardial Laser Revascularization—Morphologic Pathophysiologic And Historical Principles Of Indirect Revascularization Of The Heart Muscle" in Z Kardiol, 86(3): 147–164, March, 1997 that the transmyocardial laser revascularization results in a relevant reduction of clinical symptoms such as angina and an increase of exercise capacity in approximately two thirds of the patients treated. Objective data of enhance myocardial perfusion as assessed by positron emission tomography, thallium scans, and stress echocardiography has also been presented in other studies. Some researchers have found that TMR channels created by CO2 lasers are surrounded by a zone of necrosis with an extent of about 500 microns. In heart patients who died in the early postoperative period (1 to 7 days) almost all channels were closed by fibrin clots, erythrocytes, and macrophages. At 150 days post procedure, they observed a string of cicatricial tissue admixed with a polymorphous blood-filled capillary network and small veins, which very rarely had continuous links to the left ventricular cavity. At the 2 week post procedure point a granular tissue with high macrophage and monocyte activity was observable. See for example, the article by Krabatsch et al. entitled "Histological Findings After Transmyocardial Laser Revascularization" appearing in J. Card. Surg. 11:326–331, 1996, and the article by Gassler et al. entitled "Transmyocardial Laesr Revascularization. Historical Features In Human Nonresponder Myocardium" appearing in Circulation, 95(2): 371–375, Jan. 21, 1997.

In summary, there a number of potential mechanisms which individually or in combination may be responsible for the improvements seen in patients subjected to the previously described myocardial revascularization techniques including: (1) new blood flow through created channels, (2) angiogenesis (stimulation of the creation of new blood vessels), (3) cardiac denervation, (4) the placebo effect, and (5) ablation of ischemic myocardium.

Currently it is believed that cardiac denervation and angiogenesis are the primary causes for post procedure angina relief and improved perfusion respectively. The injury stimulates vasculargenesis and the laser energy damages nerves thereby minimizing the pain sensation. The lasers are however very expensive to purchase.

While the aforementioned techniques and methods for revascularizing the myocardium offer some promise they never the less suffer from one disadvantage or another.

OBJECTS OF THE INVENTION

Accordingly, it is a general object of this invention to provide a transmyocardial revascularization system which overcomes the disadvantages of the prior art.

It is a further object of this invention to provide a system and methodology for providing relief from ischemic myocardium.

It is a further object of this invention to provide apparatus and methods for providing myocardial perfusion that reduce the level of ischemia in a patient.

It is a further object of this invention to provide methods and apparatus for myocardial revascularization to reduce the level of discomfort associated with angina in a patient.

It is a further object of this invention to provide a device and method to enable patients that suffer from the later stages of ischemic heart disease to experience reduced pain and improved emotional well-being.

It is a further object of this invention to provide a transmyocardial revascularization system and methodology which is simple and cost effective.

It is a further object of this invention to provide an apparatus and method for myocardial revascularization to increase blood flow to the myocardium from the endocardium without using the native diseased coronary arteries.

It is a further object of this invention to provide an apparatus and method for myocardial revascularization to be used with patients having extensive coronary atherosclerosis in whom a bypass surgery is not indicated.

It is a further object of this invention is to provide a device and technique for endovascular myocardial revascularization.

It is another object of the present invention to provide methods and apparatus which can be utilized either in open surgical, minimally invasive surgical, or transluminal techniques to perfuse the myocardium.

It is a further object of this invention to provide direct myocardial revascularization without the need for opening the chest cavity.

It is a further object of this invention to provide direct endovascular myocardial revascularization without having to utilize a laser (although a laser may be used, if desired in some applications as part of the procedure).

SUMMARY OF THE INVENTION

These and other objects of this invention are achieved by providing a cardiac vascularization system and methods of revascularizing the myocardium. The system basically comprises at least one, and preferably a plurality of elongated small diameter inserts for introduction at spaced locations from one another in the wall of the myocardium. The inserts are formed of a material to elicit a foreign body or healing response to cause the formation of lumens in communication with the arterial system. The inserts may be totally resorbable, partially resorbable or non-resorbable, and in the case of the latter may be removable from the myocardium after the formation of the lumens.

In accordance with various preferred embodiments of the invention the system also includes various deployment instruments for deploying the inserts into the wall of the myocardium. Some instrument are arranged to introduce the inserts into the myocardium via either the pericardium, while other instruments are arranged to introduce the inserts into the myocardium via the endocardium.

The deployment instruments may be configured to form the lumens buy mechanical action or by the application of energy, e.g., electrical, thermal, sonic, radiation, etc., or some biological agent to the myocardium. The inserts themselves or in combination with the deployment instrument can be used to form the lumens.

In accordance with one aspect of the invention the system may include means to stabilize the deployment instrument during the formation and/or insertion of the inserts into the myocardium. In addition control means may be provided to coordinate the operation of the deployment instrument with the cardiac cycle.

DESCRIPTION OF THE DRAWING

Other objects and many attendant features of this invention will become readily appreciated as the same becomes better understood by reference to the following detailed description when considered in connection with the accompanying drawing wherein.

DETAILED DESCRIPTION OF THE PREFERRED EMBODIMENTS

Figure 1:
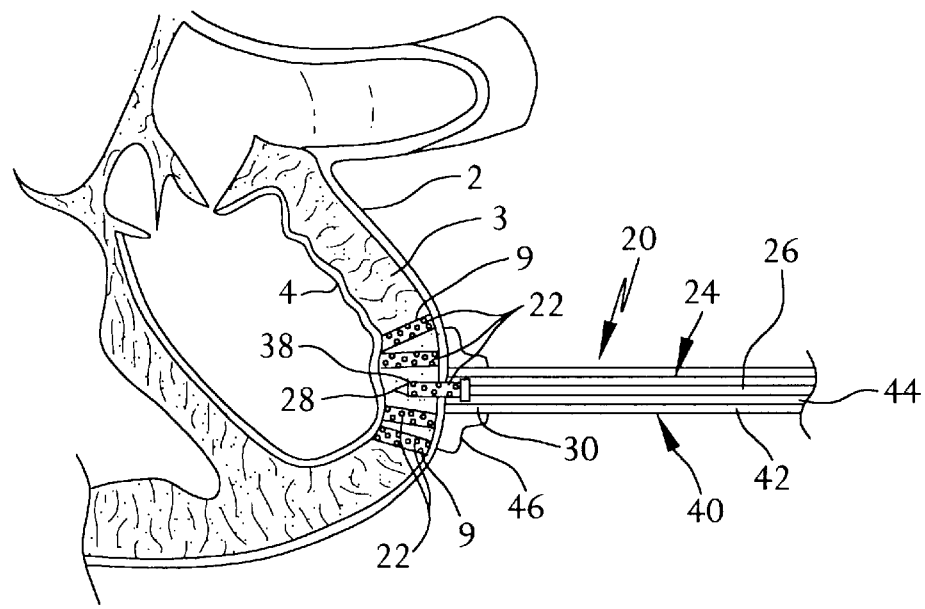
FIG. 1 is an illustration of the heart of a living human being showing one embodiment of a deployment instrument forming a portion of the myocardial revascularization system of the subject invention being used to deploy plural inserts constructed in accordance with this invention into the myocardium via the pericardium.
Figure 13:
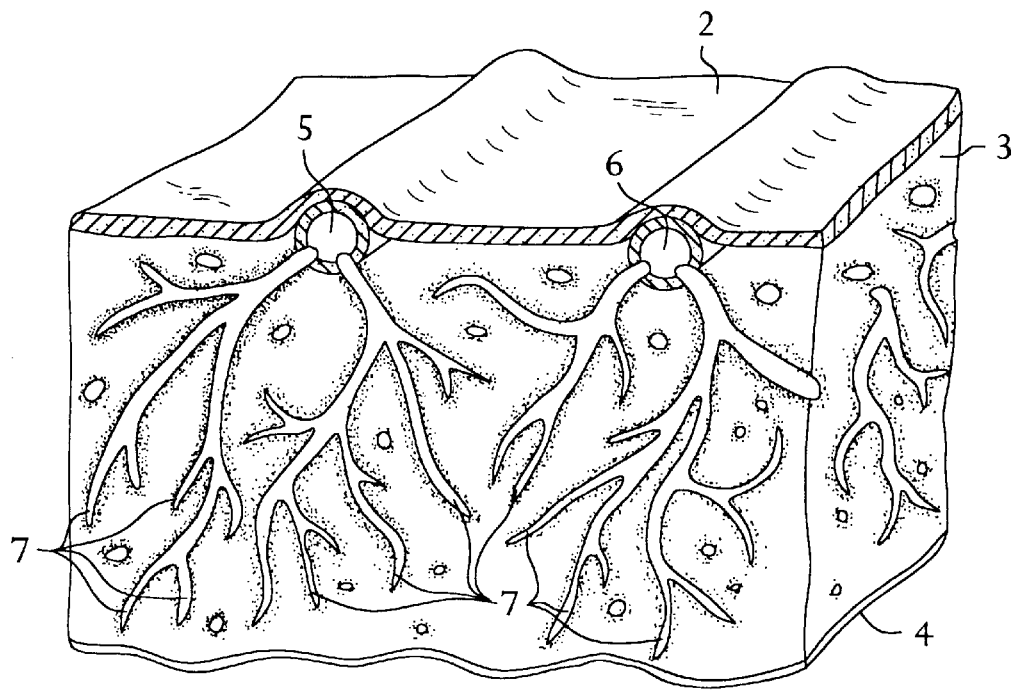
FIG. 13 is an illustration of a portion of the wall of a healthy heart showing its vascularity.
Figure 14:
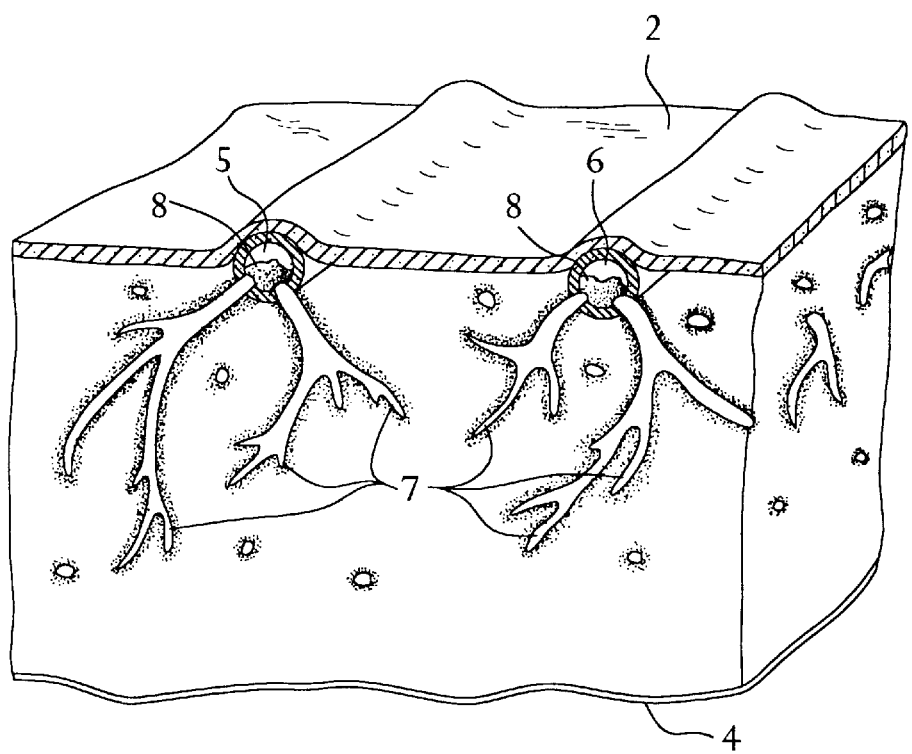
FIG. 14 is an illustration, like that of FIG. 13, but showing a wall whose vasculature has been reduced over time by atherosclerosis, e.g., the branches of its coronary arteries are fully or partially occluded and many of the capillaries in the myocardium have atrophied.

Referring now to the drawing where like reference numerals refer to like parts there is shown in FIG. 1 a transmyocardial revascularization system 20 constructed in accordance with this invention shown in the process of revascularizing the myocardium of a living, e.g., human, being. In FIG. 13 there is shown, by way of an illustration (not to scale), a section of the wall of the left ventricle of a healthy human heart 1. As can be seen therein the wall includes the epicardium 2, the myocardium 3, the endocardium 4, two unoccluded branches 5 and 6 of a coronary artery and extensive associated vasculature, e.g., capillaries 7. In FIG. 14 the illustration is of the same portion of the wall of the ventricle, but showing the effects of atherosclerosis, i.e., lesions or plaque deposits 8, in the branch vessels 5 and 6 and atrophied vasculature 7.

Figure 9A:
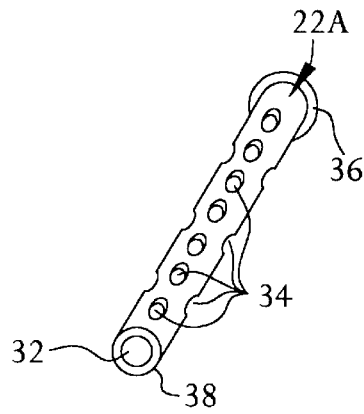
FIGS. 9A–9S are each isometric views of respective alternative embodiments of inserts constructed in accordance with this invention.

The revascularization systems of this invention are particularly suitable for revascularizing the myocardium whose blood supply has been diminished by atherosclerosis (like that shown in FIG. 14) or by other disease processes. Moreover, the subject invention contemplates various different systems and preferred ones of those systems will be described in detail later. Suffice it for now to state that each system constructed in accordance with this invention includes at least one, and preferably, a plurality of elongated inserts 22 (designated by the general reference number 22 in FIG. 1) and a deployment instrument (e.g., instrument 24 of FIG. 1) for deploying the insert(s) into the myocardium. Various alternative inserts 22A–22S are shown in FIGS. 9A–9S, respectively.

In accordance with one preferred embodiment of a system the deployment instrument 24 utilizes a piercing member (to be described later) located adjacent its distal end to create plural channels or lumens 9 (FIGS. 1 and 15) in the wall of the myocardium 3 at spaced locations from one another and into which respective inserts (e.g., inserts 22 of FIG. 1) are deployed. Other means can be utilized to form the channels or lumens 9. For example the system may include means, e.g., as part of the deployment instrument or some other device, for providing a suitable biological agent to the myocardium and associated tissue (e.g., endocardium or epicardium) to produce or form a lumen in the myocardium. Alternatively, the deployment instrument can provide one or more of various types of energy to that tissue to create the lumen(s) and then the insert(s) can be deployed therein. Examples of various types of energy contemplated for such a procedure are thermal energy, mechanical energy (e.g., rotational cutting or boring, slicing, etc), electrical energy (e.g., radio frequency energy), hydraulic energy, pneumatic energy, vibratory energy (e.g., sonic, ultrasonic, etc.) radiation energy, laser or other light energy, or other types of electromagnetic energy, etc. It should be pointed out at this juncture that the application of energy to the cardiac tissue not only serves to create the lumen(s) 9 for the insert(s) 22 and 22A–22S, but can also disable local nerves (denervation) to minimize patient pain resulting from angina.

It should also be pointed out that the formation of the channels or lumens 9 in the myocardium and associated tissue can be accomplished by means other than the insert-deployment instrument 24. In this regard the subject invention contemplates that the inserts themselves can be constructed so that they can be used to pierce or otherwise penetrate into the wall of the myocardium to form the lumens. In such applications the formation of the lumens is accomplished at the same time that the inserts are deployed therein.

Figure 2:
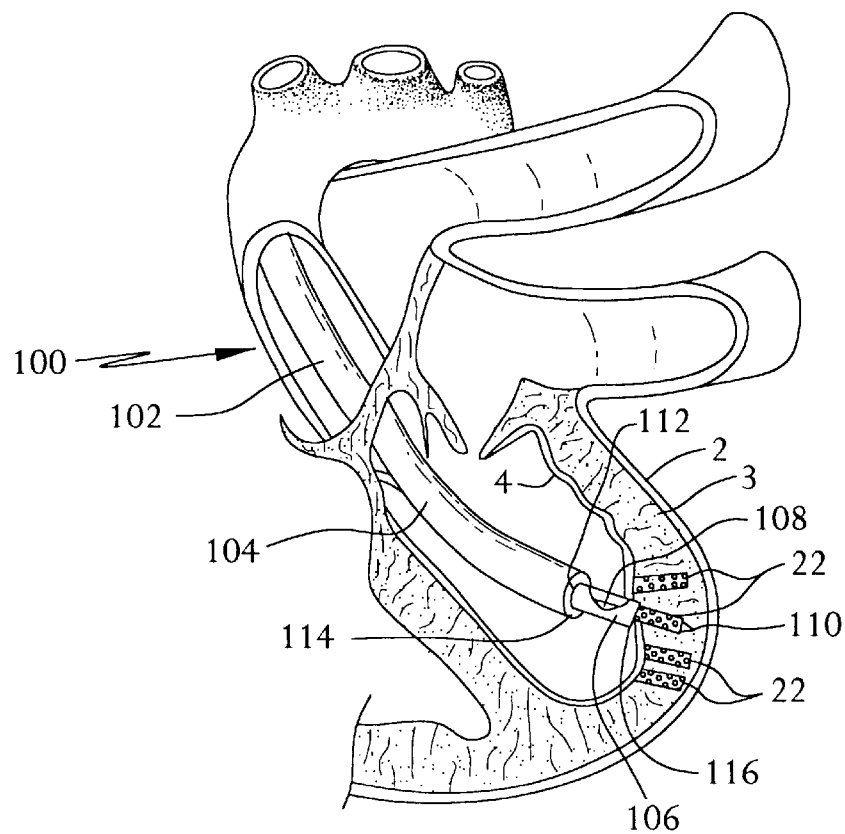
FIG. 2 is an illustration similar to that of FIG. 1, but showing another embodiment of a deployment instrument forming a portion of the myocardial revascularization system of the subject invention being used to deploy those inserts into the myocardium via the epicardium.

Irrespective of how the lumens 9 are formed, the inserts can be inserted into the wall of the myocardium 3 and into the lumens (or to form the lumens), via either a transthoracic approach to the epicardium 2 (see FIG. 1) or by a percutaneous transvascular, e.g., transfemoral, approach to the endocardium 4 (see FIG. 2). When the lumens are formed by transthoracic approach they are preferably made sufficiently deep to communicate with the interior of the ventricle. However, for some type of myocardial revascularization procedures communication of the lumen with the ventricular chamber is not necessary, as will be described later.

When the lumen(s) is(are) in communication with the ventricular chamber and the insert(s) is(are) in place within those lumens, the insert(s) serve(s) to hold the lumen(s) open and allow blood to flow into the lumen(s) from the ventricular chamber, whereupon that blood can nourish tissue and capillaries in the myocardium contiguous with the lumen.

In accordance with a preferred aspect of this invention, the inserts are formed of a material so that when they are in place they serve to initiate a "foreign body" or "healing response" in the local (i.e., contiguous) tissue, whereupon the inserts can be removed or absorbed thereafter, leaving the lumens patent to supply blood to contiguous tissue, capillaries and additional vasculature (e.g., new capillaries) which have grown over time by virtue of the process of angiogenesis. This action ensures that the myocardium receives an increased blood supply over that which it received prior to the subject transmyocarial revascularization (TMR) procedure.

Even where the lumen(s) formed do not communicate with the interior of the ventricular chamber, its (their) formation and the deployment of the insert(s) therein still has an advantageous effect insofar as providing beneficial blood flow to the myocardium is concerned. In this regard the formation of a lumen and the deployment of an insert therein serves to bridge those capillaries which are contiguous with the lumen. Thus, blood can be carried from capillaries in one portion of the myocardium to capillaries in a remote portion thereof by the lumen bridging those capillaries. In addition, over time the healing response and resultant angiogenesis induced by the presence of the inserts in the lumen will increase the myocardial vasculature, thereby further benefiting the patient.

In some applications it may be desirable to stabilize the deployment instrument against the endocardium or epicardium during the revascularization procedure. For such applications the system makes use of some releasable securement or attachment means, such as a suction hood (to be described later) to stabilize or otherwise hold the deployment instrument in place. Once positioned, the instrument can be activated to advance the piercing member or to direct energy into the cardiac tissue to create the lumen and to introduce an insert therein.

In some applications, depth control means (also to be described later) may be provided to limit the depth of penetration of the insert(s) into the myocardium. The depth control means may comprise means to limit the depth of the lumen(s) created by the instrument, or may comprise means on the insert itself to limit its depth of penetration into the lumen or may be a combination of both.

In some applications, e.g., where the deployment instrument applies electrical energy to the cardiac tissue to form the lumen(s) or where formation of the lumen(s) and/or deployment of the insert(s) therein is best accomplished during a particular portion of the cardiac cycle, the system may also include some control and sensing means (also to be described later) that synchronizes the operation of the deployment instrument to a specific portion of the cardiac cycle.

As will also be described later, the inserts 22 and 22A–22R are of various shapes, e.g., solid, tubular, trough-like, helical (spring-shaped), filament, or ribbon-like members, etc. They may be of any suitable biocompatible material, and may be formed of one or more resorbable materials so as to be either partially or totally resorbable. Examples of suitable resorbable materials are polyglycolic acid, polydiaxonone, polycaprolactone, collagen, hyaluronic acid, a polymer composite and/or oxidized regenerated cellulose.

Figure 11:
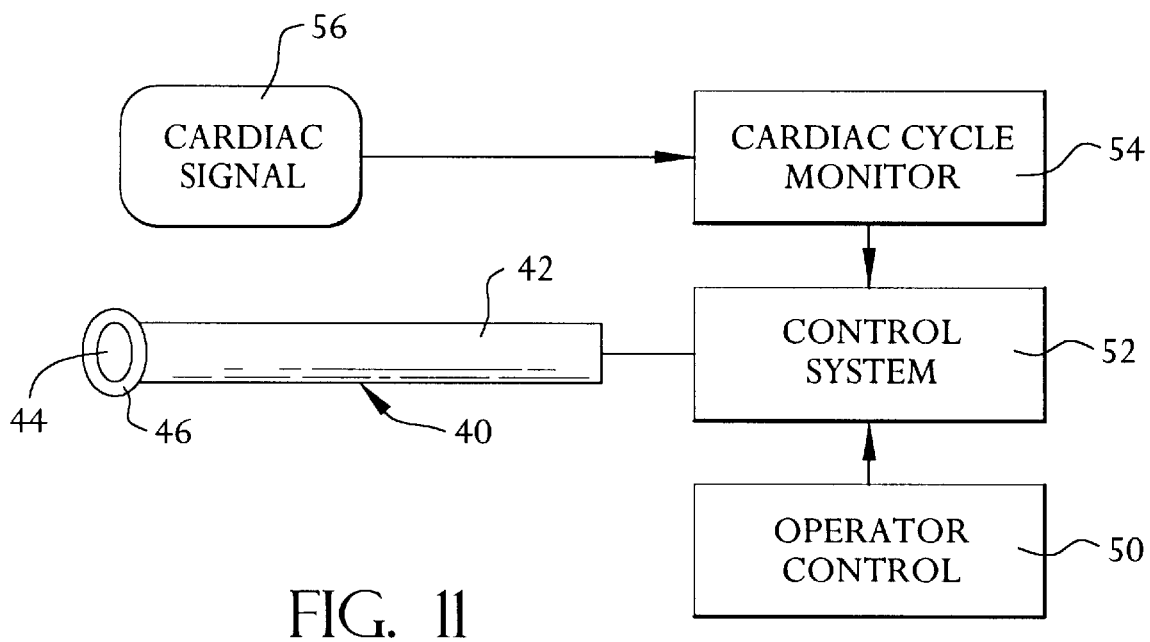
FIG. 11 is a block and schematic diagram showing one embodiment of the system of the subject invention and including means to control the operation thereof in accordance with the cardiac cycle.

Referring again to FIG. 1 the details of the system 20 as shown therein will now be discussed. As mentioned earlier that system comprises a deployment instrument 24 and plural inserts 22. The instrument 24 itself basically comprises an elongated central wire 26 having pointed or otherwise sharp distal end or piercing tip 28. A flange 30 projects outward from the periphery of the wire 26 a short distance proximally of the tip 28. The insert 22 is a tubular member which is arranged to be disposed and frictionally held on the wire 28 between the flange 30 and the tip 28 so that it can be carried by the wire 26 into the epicardium and underlying myocardium by the application of a force in the distal direction on the wire. In this regard the proximal end (not shown) of the wire 28 is coupled to means (also not shown) arranged to have a pushing force applied thereto by either manual action or by some component, e.g., a motor or other actuator, under control of a control system 52, like that shown in FIG. 11. This pushing action causes the tip 28 of the wire 26 to pierce through the epicardium and underlying myocardium to form a lumen 9 with further advancement of the wire 26 in the distal direction carrying the insert into the lumen 9.

As mentioned above, the embodiment of the insert shown in FIG. 1 and designated by the reference number 22 basically comprises a small diameter, elongated tubular member. That member is similar to the insert shown in FIG. 9A, and as best seen therein has a central channel or passageway 32 through which the wire 26 may pass when the insert is mounted thereon. The insert also includes plural apertures 34 in the wall forming it and which are in fluid communication with the passageway 32, for the reasons to be described later. An optional flange may be provided about the periphery at the proximal end 36 of the tubular insert as shown in FIG. 9A. The flange serves as a stop to engage cardiac tissue to preclude the insert from being inserted too deep into the myocardium. Insert 22 does not include the flange. The distal end 38 of insert 22 is open and is in communication with the passageway 32.

Figure 17:
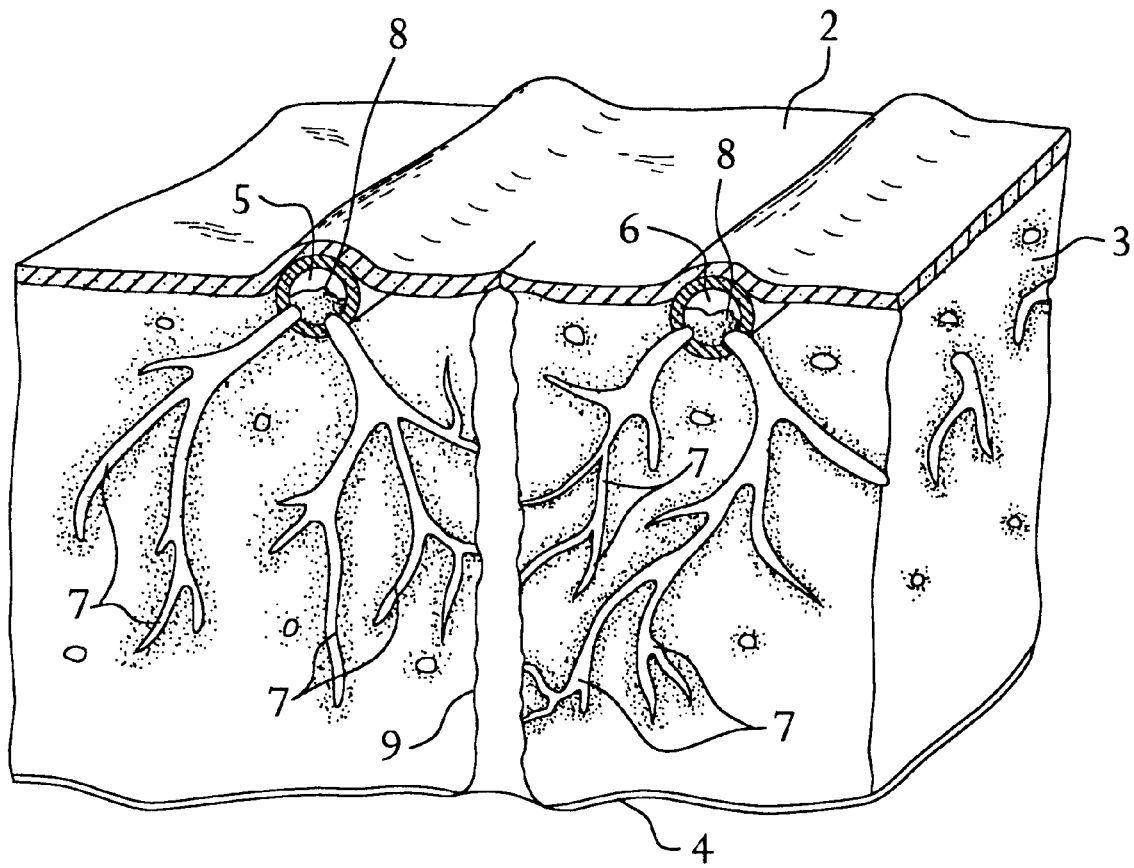
FIG. 17 is an illustration, like that of FIG. 16, but showing the wall of the heart at some later time (i.e., after the insert has been absorbed or has been removed from its lumen), whereupon the lumen may shrink in diameter but may remain patent to carry blood to contiguous tissue and capillaries, including the recently grown vasculature, to thereby provides a beneficial blood supply to the myocardium.

The insert 22 may be formed of any of the aforementioned resorbable materials so that it will be absorbed over time leaving a lumen 9 like that shown in FIG. 17. Alternatively it may be formed of a non-resorbable material. In that case it may be preferable that the insert be removable after some time to leave a lumen 9 like shown in FIG. 17.

When the insert 22 is located on the deployment instrument's wire 26 its proximal end 36 (FIG. 9) is in abutment with the flange 30 on the wire and with the piercing tip 28 of the wire extending out of the distal end 38 of the insert as shown in FIG. 1. As mentioned above, the proximal end of the wire 26 is coupled to means to have a pushing force applied thereto manually or under control of a control system 52 like that shown in FIGS. 11 or 12. This pushing action causes the tip 28 of the wire 26 to pierce through the epicardium and underlying myocardium to start to form a lumen 9. At the same time the flange 30 on the wire abuts the proximal end 36 of the insert to push the insert along with it to carry the insert into the lumen 9 as it is formed. The stop on the insert (if incorporated into the insert) or the flange 30 of the wire 26 is arranged to enable the proximal end of the insert to pass through the epicardium and just slightly into the underlying myocardium and with the length of the insert 22 being selected so that the open distal end 38 of the insert just enters the ventricle. To that end, the length of the insert is preferably selected to be consistent with the thickness of the myocardium into which it is implanted. In order to accommodate various thicknesses of myocardia, the inserts of the subject invention may be pre-cut to any length in the range of approximately 0.6 cm to 2.0 cm in length. Moreover, for typical application the inserts preferably have an outside diameter in the range of approximately 1.5 mm to 2.5 mm and an inside diameter in the range of approximately 1.0 to 2.0 mm.

Figure 12:
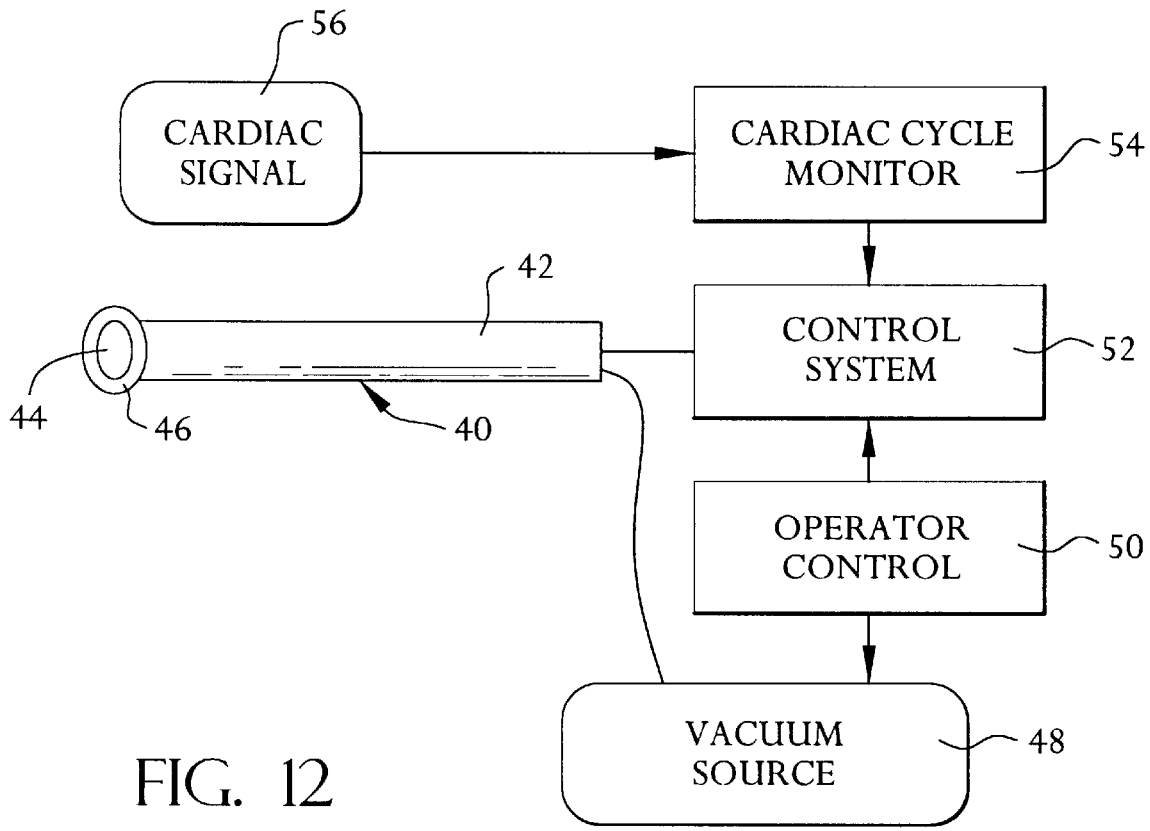
FIG. 12 is a diagram like that of FIG. 11 but showing the addition of a mechanism, e.g., a vacuum hood, for use with a deployment instrument of this invention to stabilize the deployment instrument with respect to the myocardium.

In order to stabilize the deployment instrument 24 during the lumen forming-insert deployment procedure, the device 24 of the system may be constructed like shown in FIGS. 1 and 12 to include a releasably securable attachment mechanism in the form of a suction hood 40 and associated components. The suction hood 40 basically comprises an elongate tube 42 having a central passageway 44 for accommodating the insert deployment wire 26 with the insert 22 mounted on the distal end thereof. An enlarged flange 46 extends about the periphery of the distal end of the tube 42 for engagement with the epicardium. A source of vacuum 48 (FIG. 12) is coupled to the proximal end of the tube 42. The vacuum source is arranged to be actuated by operation of the operator control 50 (FIG. 12). This action couples the vacuum source 48 to the interior of the tube 42 to produce suction at the distal end of the hood to hold the hood in place on the pericardium centered over the location at which an insert is to be deployed. The operator control 50 can then be activated to cause the control system 52 and its various components to operate to effect the pushing of the deployment instrument's wire 26 (with the insert 22 mounted thereon) distally into the epicardium and underlying myocardium, as discussed above.

If it is desired to time the introduction of the insert 22 into the myocardium to any particular portion of the cardiac cycle, e.g., during diastole, then the system may include use of a cardiac cycle monitor 54 and an associated cardiac sensor 56. The cardiac sensor 56 can be any suitable conventional device for providing an electrical signal indicative of the cardiac cycle. The cardiac cycle monitor is responsive to the sensor for providing signals to the control system 52, which controls the operation of the deployment instrument in coordination with the sensed cardiac cycle.

Thus, the control system initiates the operation of means in the system coupled to the wire 26 to push the wire distally at a predetermined point in the cardiac cycle.

After each of the inserts 22 has been deployed into the myocardium, the instrument is removed, i.e., the wire 26 extracted, and the insert 22 left in place. Thus, since the distal end 38 of the insert 22 is open and in fluid communication with the interior of the left ventricle blood from the left ventricular chamber can flow into the distal end of the insert and be carried down its central passageway 32 and out through the apertures 34 into the adjacent myocardial tissue and capillaries. Since the proximal end of the insert is preferably located just under the epicardium, when the insertion wire 26 is withdrawn the puncture in the epicardium through which the insertion wire passed will close off and hemostasis will occur shortly thereafter. This action will prevent the leakage of blood out of the lumen 9 through the epicardium.

As will be appreciated by those skilled in the art the shape of the insert 22 (as well as all of the other inserts of this invention) will keep the lumen 9 in which it is located open to the flow of blood therethrough. Over time the body's natural healing response to the "foreign" insert deployed within the lumen 9 will result in increased vasculature contiguous with the lumen, like shown in FIG. 17. It should be noted that in FIG. 17 the relevant cardiac portion is shown after the insert has either been absorbed or removed, but the result is the same, namely, the formation of new capillaries and vessels as a result of the body's natural healing response and angiogenesis caused by the one-time presence of the insert within the lumen.

Figure 15:
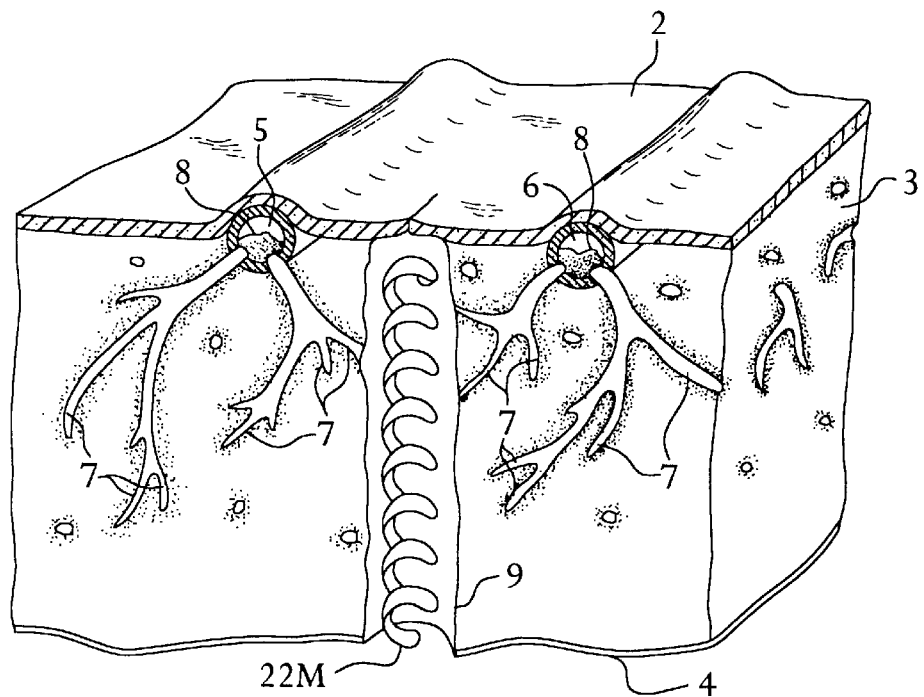
FIG. 15 is an illustration, like that of FIG. 14, but showing the wall of the heart immediately after deployment of an insert of the system of this invention in the myocardium to increase the flow of blood from the ventricle via the lumen in which the insert is located to tissue and capillaries contiguous with the lumen.
Figure 16:
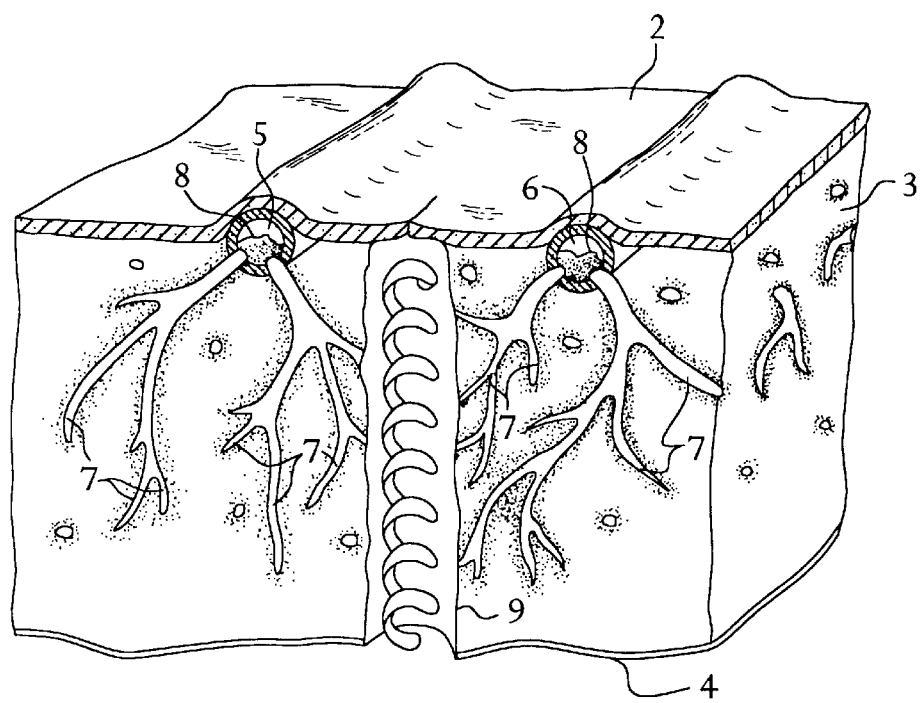
FIG. 16 is an illustration, like that of FIG. 15, but showing the wall of the heart some time after the deployment of an insert so that the insert has elicited a foreign body response in the myocardium tissue to stimulate angiogenesis and revascularization, whereupon the increased flow of blood in one portion of a vessel can provide added blood to neighboring tissues and capillaries.

In FIGS. 15–17 the revascularization of the myocardium of an atherosclerotic diseased heart is illustrated. In particular, in FIG. 16 there is shown the same portion of the heart shown in FIG. 14, and described earlier, but after a lumen 9 has been formed in the myocardium and an alternative embodiment of an insert located within that lumen. The alternative insert is the embodiment of the insert shown in FIG. 9M and designated by the reference number 22M. The details of this insert will be described later. Suffice it for now to state that insert 22M is in the form of a cylindrical coil or helix and has been inserted a lumen 9 formed in the same manner as described earlier. Since the insert 22M is a helix, it will hold the lumen 9 open and in communication with the interior of the ventricle at its distal end. Moreover, blood can flow into the lumen through the center of the insert 22M and out through the spaces between contiguous coils to feed the contiguous myocardial tissue and capillaries. On the short term any capillaries which receive blood from the lumen 9 can carry that blood to remote locations, thereby nourishing the tissue at such remote locations by the delivery of more blood thereto than prior to the procedure. Over time the body's natural healing response and angiogenesis will result in increased vasculature, such as shown in FIG. 16.

FIG. 17 shows the condition after angiogenesis has occurred to create significant new vasculature, e.g., capillaries 7, and the insert 22 either has been removed or resorbed by the body. The resorption or removal of the insert from the lumen, so that the insert is no longer present to hold the lumen open, may permit the lumen to shrink or otherwise decrease somewhat in diameter, as illustrated in FIG. 17, or eventually close. Even if the lumen 9 eventually closes there will still be some beneficial effect since the tissue contiguous with the lumen 9 will be more highly vascularized than prior to the insertion of the insert due to the elicited angiogenesis.

As should be appreciated from the foregoing whether the system 20 makes use of non-resorbable or resorbable inserts is of little relevance from the standpoint of immediately increased blood flow to the myocardium tissue and capillaries contiguous with the lumens so long as the inserts are constructed to enable blood to flow therethrough or therearound in the lumens from the interior of the ventricular chamber. If, however, the inserts are constructed so that they do not allow blood to flow therethrough or therearound within the lumens, then the beneficial effects, e.g., increased vasculative, of the inserts will not likely arise until after they have induced the natural healing response in the myocardium and have been absorbed or otherwise removed from the myocardium.

Figure 3:
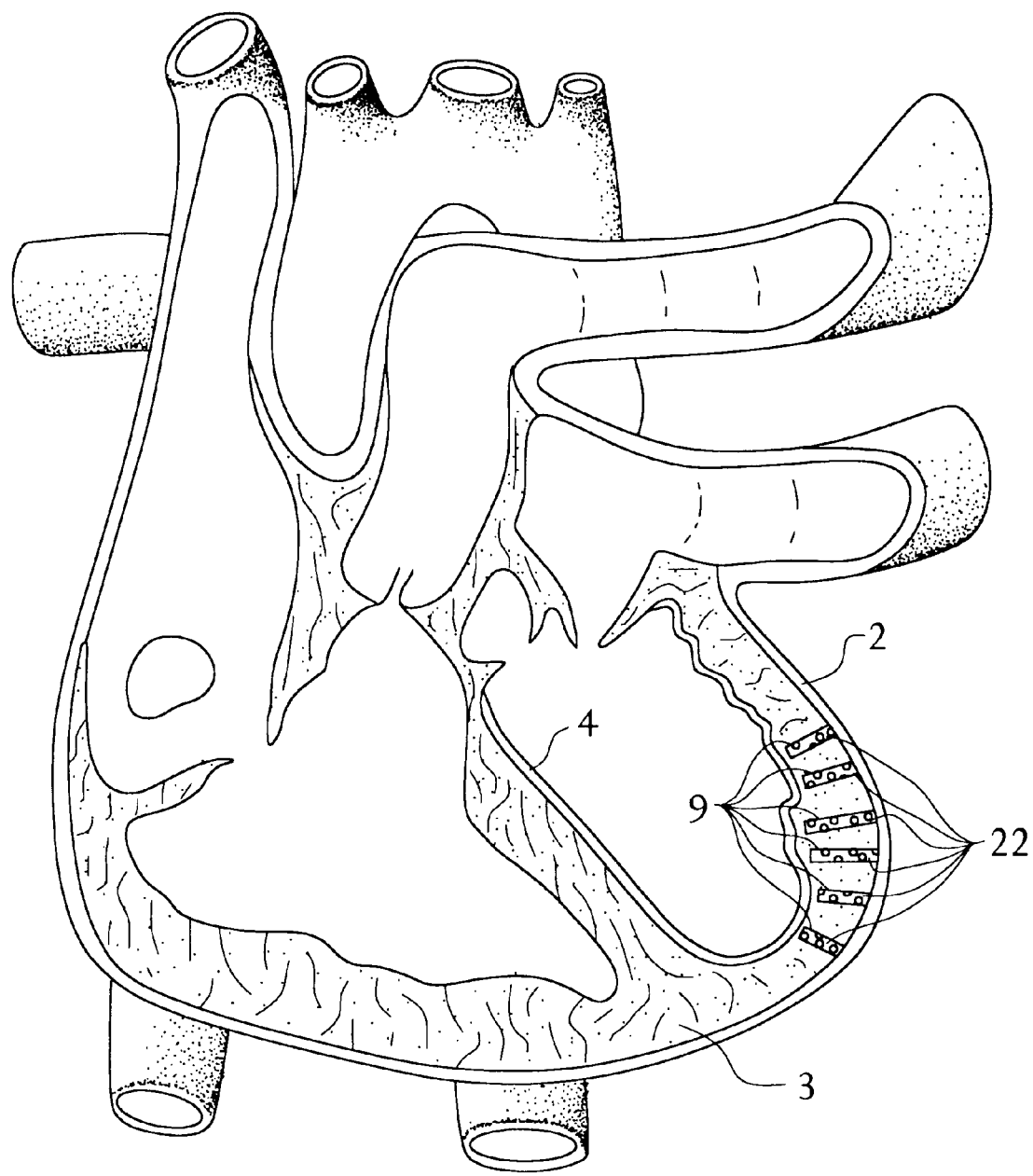
FIG. 3 is an enlarged illustration of the heart of a living human being showing the inserts of the system of FIG. 1 in place fully embedded in the wall of the myocardium.

It should be pointed out at this juncture that for some applications the inserts may be constructed so that they do not extend into communication with the ventricular chamber to permit blood to flow from the ventricle into the lumen. One such alternative arrangement is shown in FIG. 3. In that illustration the inserts 22 are shown as being fully located (embedded) within the myocardium. Since there will be no blood flow into the lumens from the ventricular chamber, this arrangement will not serve to immediately increase the amount of blood available to the myocardium tissue in which the inserts 22 are located. However, if the inserts are constructed so that blood can flow either through them (e.g., they include a longitudinal passageway and sidewall apertures like those described earlier, or are porous, etc.) or around them within the lumen, then blood from tissue and/or capillaries contiguous with one portion of the lumen 9 can be carried to other portions of the lumen and the tissue and capillaries contiguous therewith. Thus, the presence of the inserts in the lumens may serve to bring blood from one portion of the myocardium to other portions. Moreover, the angiogenesis action resulting by the location of the inserts within the lumens over time will further revascularize the myocardium.

In FIG. 2, a system 100 constructed in accordance with this invention is shown during the process of revascularizing the myocardium via a transvascular access to the endocardium and myocardium. The system 100 comprises a small diameter, flexible deployment instrument 102 and one or more inserts constructed like those described heretofore. In particular, in the example shown in FIG. 2, the inserts used are the inserts 22. The instrument 102 comprises an outer tube or catheter 104, an inner tube 106, and a flexible wire 108. The wire 108 has a pointed distal end or piercing tip 110. The catheter 104 includes a central passageway 112 extending down its length and terminating at a free end in the form of a rounded or non-sharp tip 114. The inner tube 106 is disposed within the passageway 112 and is movable longitudinally with respect to the catheter 104. The inner tube 106 includes a central passageway through which the wire 108 extends, with the tip 110 of the wire extending beyond the free end 116 of the inner tube by a distance just slightly greater than the length of an insert 22.

The insert 22 is located on the extending portion of the wire 108 as shown in FIG. 2. When introduced through the vascular system and into the heart the inner tube 106 and wire 108 are fully retracted within the catheter 104 but located adjacent its tip 114. The rounded tip 114 of the catheter serves as the end of the instrument 102 to facilitate its safe guidance to the operative position shown in FIG. 2. At that time the inner (pusher) tube 106 with the wire 108 extending therethrough is pushed distally by some means, e.g., manually or by some activator forming a portion of the control system 52, so that the wire's tip 110 penetrates through the endocardium and into the myocardium. The continued pushing action forms the lumen and carries the insert into the lumen 9 in a similar manner as described earlier. When the insert is in the desired position within the myocardium the wire 108 is retracted with respect to the inner tube 106 until it no longer is within the insert, thereby depositing the insert within the lumen 9. The instrument can then be used to deploy other inserts 22 in the same manner, and once all have been deployed the instrument is retracted as a unit from the heart and out of the associated vascular access path.

In FIGS. 4–8 there is shown another alternative system 200 (FIG. 5) for effecting the revascularization of the myocardium. The system 200 is of manual type and basically comprises at least one insert 22R, like that shown in FIG. 9R, and a manually operated deployment instrument 202 for deploying the insert in a lumen in the myocardium. The insert 22R basically comprises a resorbable suture 204 or other flexible filament having a distal end at which a barbed resorbable anchor 206 is fixedly secured. The anchor includes a rounded distal end 208 (FIG. 8) from which plural fingers 210 project backward. The fingers may be somewhat flexible to facilitate the disposition of the insert within the instrument 202 (as will be described later).

Figure 4:
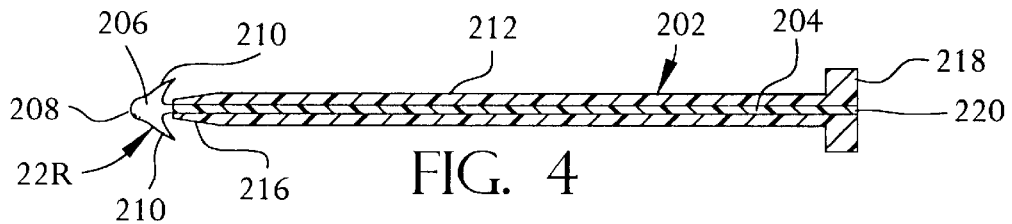
FIG. 4 is a side elevational view, partially in section, of an alternative embodiment of an insert and an alternative deployment instrument forming an alternative embodiment of a system constructed in accordance with this invention.

The instrument 202 basically comprises a pusher member 212 and a piercer member 214. The pusher member 212 is in the form of a small diameter tube having a tapered distal end 216, a flanged proximal end 218 forming a cap, and a central passageway 220 extending therebetween. The suture or filament portion 204 of the insert 22R is located within the passageway 220, with the anchor 206 being located immediately distally of the tapered distal end 216 of the pusher as shown in FIG. 4.

Figure 5:
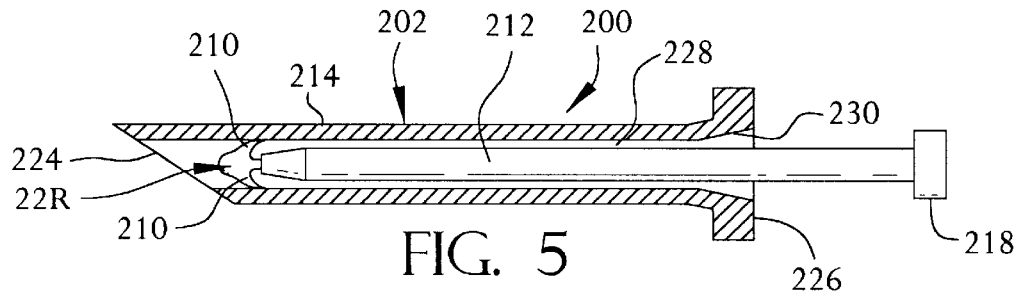
FIG. 5 is a side elevational view, partially in section, showing another portion of the deployment instrument of the embodiment of the system shown in FIG. 4.

The piercer member is a small diameter tube having a bias-cut distal end to form a piercing tip 224, a flanged proximal end forming a handle 226, and a central passageway 228 extending therebetween. The entrance to the passageway 228 is flared at 230. The inside diameter of the passageway 228 is slightly greater than the outside diameter of the pusher member 204 so that the pusher member can be located therein, with the fingers 210 of the anchor position 206 of the insert 22R flexed radially inward to enable the anchor to fit within the passageway 228 as shown in FIG. 5.

Figure 6:
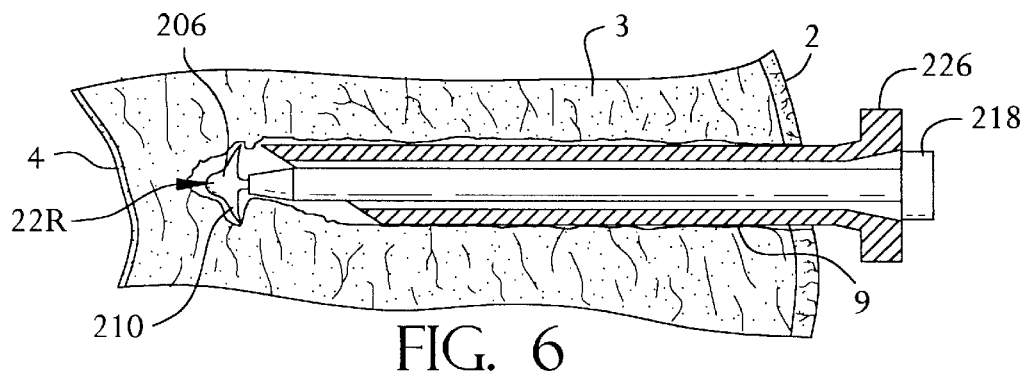
FIG. 6 is a side elevational view, partially in section, showing the deployment of the insert of FIG. 4 into the wall of the myocardium by the deployment instrument of FIGS. 4 and 5.
Figure 7:
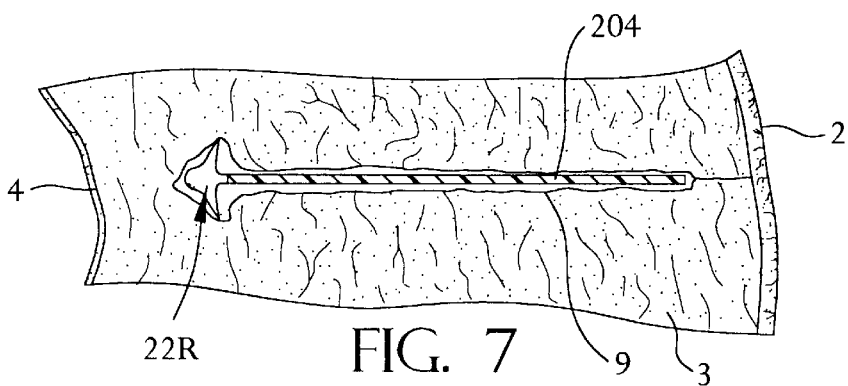
FIG. 7 is a side elevational view, partially in section, showing the insert of FIGS. 4–6 when fully deployed in the wall of the myocardium.
Figure 8:
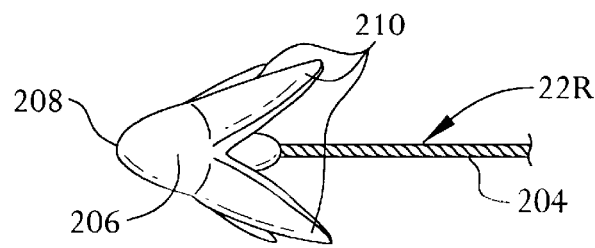
FIG. 8 is an enlarged isometric view of the distal end of the insert shown in FIGS. 4–7.

The instrument 202 is particularly suitable for transthoracic introduction into the myocardium 3. To that end the instrument 202 is assembled as shown in FIG. 5 and manipulated (i.e., pushed distally) such that the needle's piercing tip 224 pierces the epicardium 2 and enters to a desired depth into the myocardium 3 to form a lumen 9. As shown in FIG. 6 the depth of penetration is less than the thickness of the myocardium so that the lumen 9 is not in communication with the interior of the ventricular chamber (although it could extend therein, if desired). Stop means (not shown) forming a portion of the instrument 202 can be provided to establish the desired depth of cardiac penetration.

Once the piercer member is at the desired depth, the cap 218 of the pusher member is pushed distally with respect to piercer member's handle 226 to extend the insert's anchor 206 into the lumen tract, whereupon the freeing of the anchor's fingers 210 allows them to flex outwardly as shown in FIG. 6. The pusher member 212 and the piercer member 214 are then withdrawn as a unit proximally, so that the filament portion 204 is freed leaving the insert in place like shown in FIG. 7. The anchor of the insert serves to secure it within the lumen 9 resistant to accidental dislodgment during the deployment procedure. It should be pointed out that the anchor can take various forms, e.g., be a rigid barb-like member lacerated on the outer portion of the insert or it can be an activatable pivoting member (not shown) similar in construction to that used on a conventional clothing label tag, or any other suitable construction.

The filament portion 204 may consist of a solid filament, such as a PGA suture, or a strip of material, such as collagen or Gelfoam, or may be non-resorbable, like Gortex. In any case the material for the filament portion 204 is selected to initiate a foreign body reaction to stimulate arteriogenesis in a manner similar to that described earlier.

It must be pointed out at this juncture that each insert of this invention is preferably configured such that its presence in the myocardial tissue does not significantly limit the contractility of the cardiac muscle, although as will be described later some embodiments provide less resistance to cardiac contractility than others. Moreover, the inserts may be coated with or contain growth factors, anti-oxidants, seeded cells, or other drug/biologically active components depending upon the result desired.

Referring now to FIGS. 9A to 9S, the details of other inserts constructed in accordance with this invention will be described. These inserts are merely exemplary of many other inserts which can be constructed to accomplish the ends of this invention.

The embodiment of the insert 22A shown in FIG. 9A is a tubular structure with axial perforations 34 for allowing blood to pass through the longitudinal passageway 32 and to pass through the lateral perforations 34 into the adjacent myocardium.

Figure 9B:
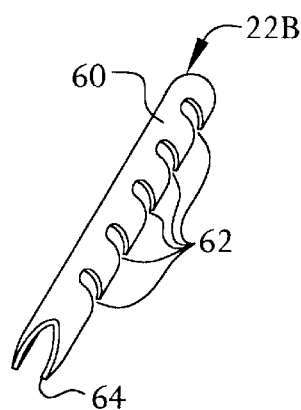

The embodiment of the insert 22B shown in FIG. 9B is a trough-like structure 60 with slots 62 in the marginal edges to form fins for holding the lumen 9 open. The slots 62 allow more contact of the blood to the neighboring myocardium. The tip 64 is sharpened to facilitate the deployment, e.g., it helps pierce the cardiac tissue during deployment.

Figure 9C:
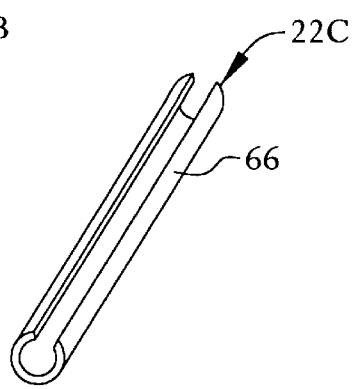

The embodiment of the insert 22C shown in FIG. 9C is a simple trough-like structure 66, that is relatively easy to manufacture, e.g., can be made by die cutting a rectangular sheet and forming the sheet around a pin.

Figure 9D:
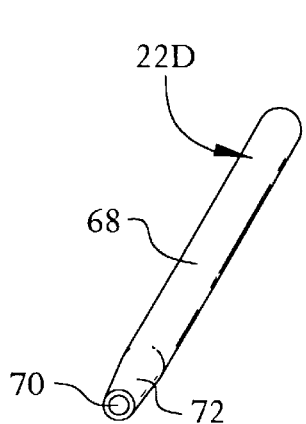

The embodiment of the insert 22D shown in FIG. 9D comprises a porous walled tube 68, with a longitudinal passage 70 extending down its center and whose distal end 72 is open.

Figures 9E, 9F:
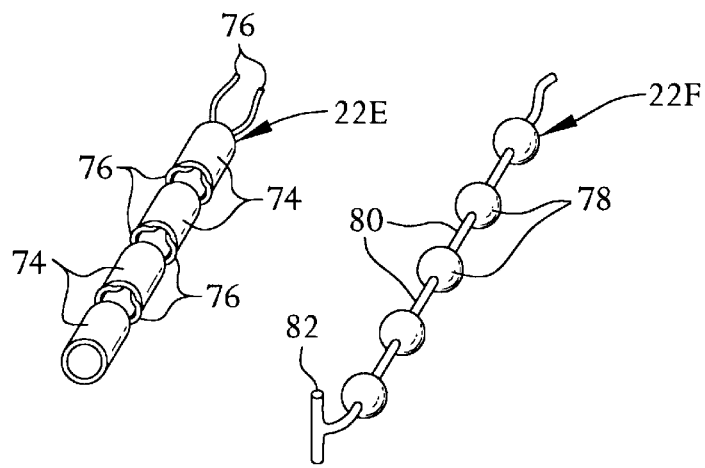

The embodiment of the insert 22E shown in FIG. 9E is a series of tubular cylindrical sections 74 that are connected by flexible filaments 76. This structure effectively stents the lumen opening and allows the insert to freely contract and expand along the longitudinal axis and therefore conform to the contraction of the myocardium during the cardiac cycle.

The embodiment of the insert 22F shown in FIG. 9F is formed of several spherical beads 78 spaced on a flexible filament 76. The filament also incorporates a T-shaped distal end in the form of anchor member 82 to aid in placement or securement. This insert also effectively stents the lumen and allows the insert to freely contract and expand along the longitudinal axis and therefore conform to the contraction of the myocardium during the cardiac cycle.

Figure 9G:
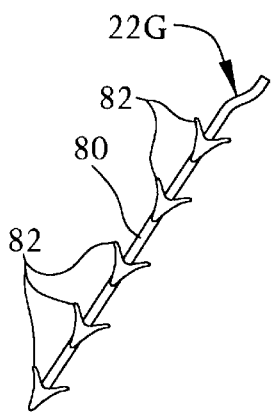

The embodiment of the insert 22G shown in FIG. 9G is similar to that shown in FIG. 9F except that the periodically spaced barb structures 82 extend outward from the filament 80 at spaced locations. This arrangement may better anchor the insert in the myocardium and may also allow for better fluid communication past each barb structure along the length of the lumen 9 than the embodiment 22F of FIG. 9F.

Figure 9H:
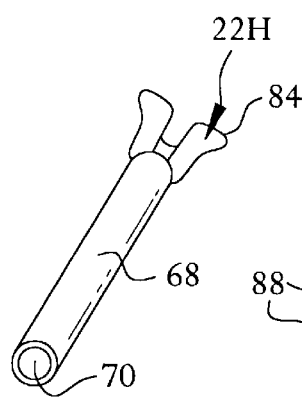

The embodiment of the insert 22H shown in FIG. 9H is a cylindrical porous material tube 68 with a proximal end in the form of a shoulder 84 to limit penetration. This particular embodiment appears best suited for insertion from the endocardium into the myocardium, whereupon the shoulder 84 anchors the opening of the insert at the ventricle.

Figure 9I:
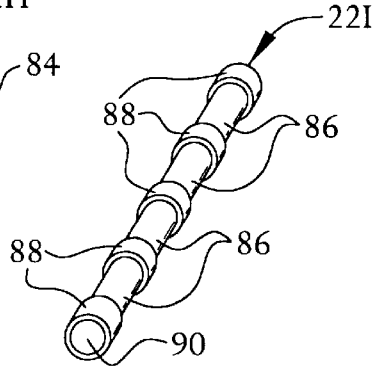

The embodiment of the insert 22I in FIG. 9I is a flexible woven tube 86 having plural equidistantly spaced reinforcing rings 88. The woven portions of the tube are porous to allow blood to pass from the inner passageway 90 for communication with the blood vessels and capillaries contiguous with the other lumen 9. The reinforcing rings 88 support the insert and the adjacent myocardium to keep the lumen from collapsing.

Figure 10A:
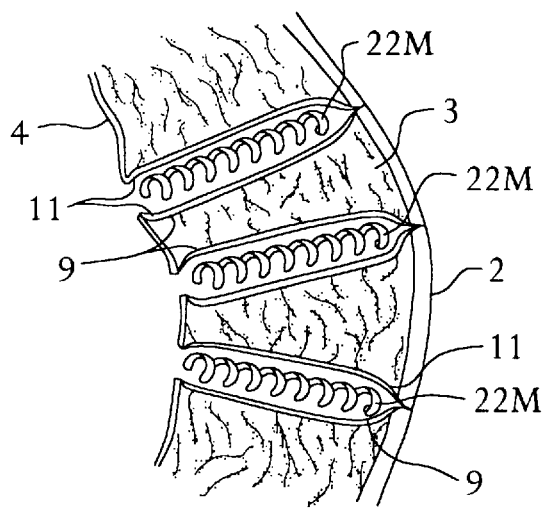
FIGS. 10A–10D are each side elevational view, partially in section, of various exemplary inserts of the subject invention shown in place within the wall of the myocardium.
Figure 10B:
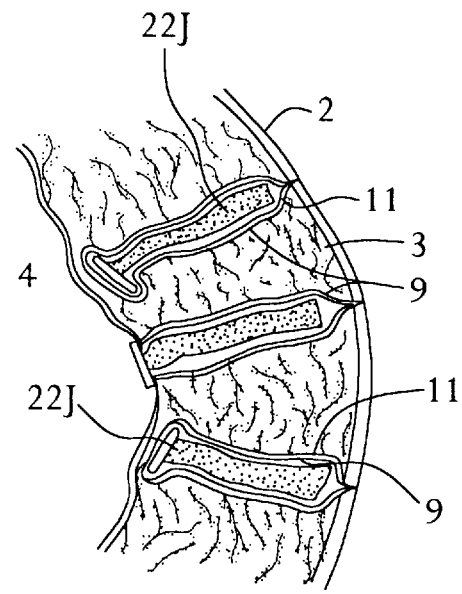
Figure 10C:
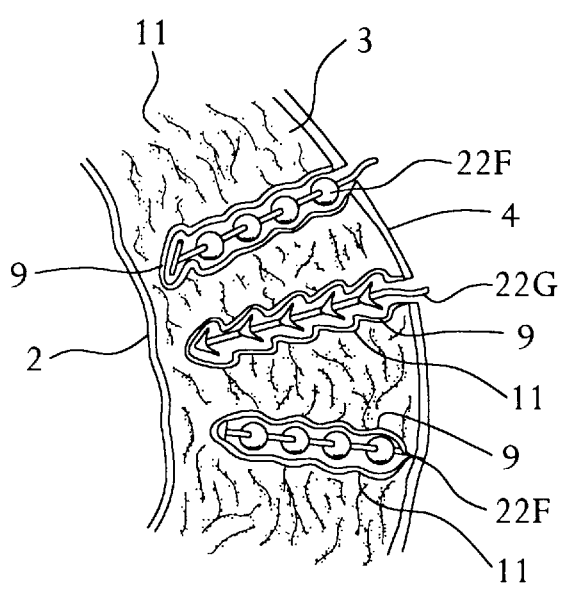

The embodiments of the inserts 22J, 22K, and 22L shown in FIGS. 9J, 9K and, respectively, consist of flexible ribbon-like structures 22 with anchors 94, 96, and 98, respectively, on the distal end for locating and securing the inserts into the myocardium. The ribbon-like material can be formed of materials such as woven dacron, polyglycolic acid, cotton, silk, and collagen. The ribbon-like tail of these embodiments can be made extra long and after implantation during a surgical approach whatever portion extends from the epicardium can be trimmed off (see FIG. 10B). The anchor portion can be formed by insert molding the anchor component onto the filament structure. The main feature of these constructions is to stimulate a foreign body reaction and a healing response which results in the formation of capillaries at the site of the implant. As such, these structures will provide less of a short term improvement to vascularization, but instead will lead to a long term improvement.

The embodiment of the inserts 22M, 22N, and 22O shown in FIGS. 9M, 9N, and 9O, respectively, consists of helical coil-like structures 120. The implants can be formed of such materials as stainless steel, nitinol, titanium or such material as polyglycolic acid or polylactic acid. The embodiments are flexible, particularly with respect to their longitudinal axis and as such will readily deform longitudinally in conjunction with the cardiac cycle of the myocardium. These structures serve to stent the lumen 9 and allow for excellent fluid communication between the lumen 9 and the adjacent blood vessels. The embodiments shown in 9N and 9O have anchoring portions at their respective distal ends which can be used to locate and secure the inserts in the myocardium. In particular, the insert 22N includes a hook-like member 122 at its distal end, whereas the insert 22O includes a plate-like anchor 124 at its distal end.

The embodiment of the insert 22P shown in FIG. 9P is a flexible filament-like member 126 with a stiffened distal end portion bent back over itself for anchoring the insert into the myocardium. This insert functions in a similar manner to the inserts of embodiments 22J, 22K and 22L.

Figure 10D:
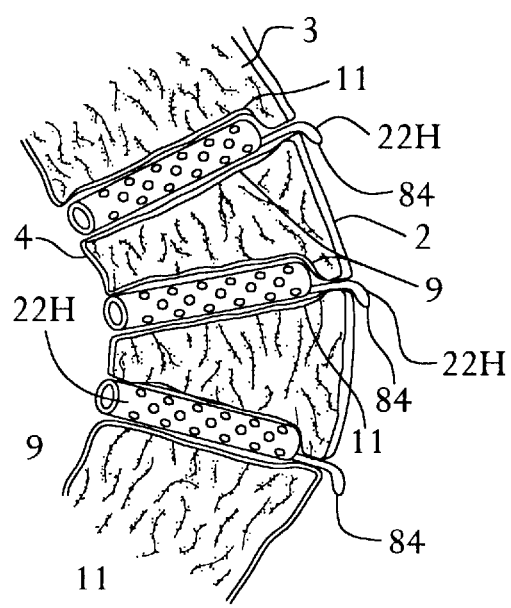

The embodiment of the insert 22Q shown in FIG. 9Q is a perforated cylinder member, similar to insert 22A but with tongue-like member 130 at the proximal end of the cylinder to form a shoulder. The shoulder serves to limit the depth of placement of the insert into the myocardium. This particular embodiment is particularly suited to being placed through the epicardium into the myocardium. The bulbous portion of the shoulder limits the depth of penetration into the myocardium and the epicardium seals around it to prohibit leakage from the channel past the epicardium like shown in FIG. 10D.

The embodiment of the insert 22R shown in FIG. 9R has been described earlier. This insert 22R functions in a similar manner to inserts 22J, 22K and 22L. Moreover, the filament-like tails of these embodiments can be made extra long to be trimmed off in a similar manner to that described earlier with reference to inserts 22J, 22K and 22L. The filament can be formed of Dacron, polyester, silk, polyglycolic acid, collagen, or some other such suitable material. The main feature of these constructions is to stimulate a foreign body reaction and a healing response which results in the formation of capillaries at the site of the implant. As such, these structure will provide less of a short term improvement to vascularization, but instead will lead to a long term improvement.

The embodiment of the insert 22S shown in FIG. 9S is a "flowable" insert comprised of a flowable material 132, such as collagen paste, cyanoacrylate (glue/adhesive), thrombin glue, growth factor gelatin, etc. The flowable material can be stored in a tube (not shown) and dispensed into the puncture tract by a needle-like device, such as a syringe (not shown). The flowable material can be designed to harden slightly after placement, like an epoxy or silicon caulking material, so that it is not extruded from the puncture during the cardiac contraction cycle. A main feature of this construction is to stimulate a foreign body reaction and a healing response which results in the formation of capillaries at the site of the implant. As such, the insert 22S will provide less of a short term improvement to vascularization, but instead will lead to a long term improvement.

In FIGS. 10A to 10D various of the inserts described above are shown in place in the myocardium to cause the body to initiate a healing response in tissue contiguous with the lumen, as described heretofore. The tissue at which the foreign healing response occurs at initially is designated by the reference number 11 in those figures. While not shown in FIGS. 10A–10D, additional or new vasculature results in the myocardial tissue as a result of angiogenesis Without further elaboration the foregoing will so fully illustrate our invention that others may, by applying current or future knowledge, adopt the same for use under various conditions of service.

What is claimed is:

1. A system for vascularizing a selected portion of the myocardium of the heart of a living being, said system comprising a plurality of elongated inserts and an instrument for deploying said inserts, at least a portion of each of said inserts being formed of a resorbable material, said inserts being arranged for introduction at spaced locations from one another within the selected portion of the myocardium the selected portion of the myocardium having a plurality of channels formed therein, said instrument being arranged to deploy said inserts within respective ones of the channels, said inserts being constructed so that when they are deployed within the channels they do not significantly limit the contractility of the being's heart, said inserts also being of a size to substantially fill the channels until resorbed, said resorbable material of said inserts eliciting a foreign body or healing response in the tissue making up the selected portion of the myocardium to enhance to flow of blood therein.

2. The system of claim 1 wherein each of said inserts is formed entirely of a resorbable material.

3. The system of claim 1 wherein said inserts are arranged to enable blood to flow therethrough.

4. The system of claim 3 wherein said inserts are porous.

5. The system of claim 1 wherein said system includes means to limit the depth of penetration of said inserts into the myocardium.

6. The system of claim 1 wherein said instrument is arranged to be inserted into the interior of the heart to introduce said inserts into the myocardium via the endocardium.

7. The system of claim 1 wherein said instrument is arranged to be inserted into the chest cavity to introduce said inserts into the myocardium via the epicardium.

8. The system of claim 1 wherein said system includes piercing means for producing the channels in the myocardium.

9. The system of claim 8 wherein said instrument is arranged to deploy said inserts into respective ones of the channels after the formation thereof.

10. The system of claim 8 wherein said instrument includes said piercing means and wherein said instrument is arranged to deploy said inserts into respective ones of the channels.

11. The system of claim 8 wherein each of said inserts is arranged to pierce the myocardium to produce a respective one of the channels.

12. The system of claim 8 wherein said piercing means comprises a member arranged to mechanically pierce into the myocardium to produce the channels.

13. The system of claim 8 wherein said piercing means comprises means for applying energy to the myocardium to produce the channels.

14. The system of claim 13 wherein said energy is selected from the group consisting of one or more of mechanical, electrical, thermal, electromagnetic, vibratory, hydraulic, pneumatic, and nuclear energy.

15. The system of claim 14 wherein said piercing means comprises means for applying a biologically active material to the myocardium to result in the production of the channels.

16. The system of claim 1 wherein each of said inserts comprises an anchor portion for anchoring it in position within the myocardium.

17. The system of claim 16 wherein each of said inserts additionally comprises an elongated portion coupled to said an anchor portion.

18. The system of claim 17 wherein said elongated portion comprises a filament.

19. The system of claim 1 additionally comprising means for monitoring the cardiac cycle and for coordinating the operation of said deployment means with the cardiac cycle.

20. The system of claim 1 wherein said system includes stabilizing means for stabilizing the position of said deployment means adjacent the myocardium during the deployment of said inserts.

21. The system of claim 1 wherein said inserts additionally comprises one or more of the group consisting of pharmaceuticals, biologically active materials, growth factors, radioactive materials, and radiopaque materials.

22. The system of claim 1 wherein said instrument is arranged to provide one or more of the group consisting of pharmaceuticals, biologically active materials, growth factors, radioactive materials, and radiopaque materials.

23. The system of claim 1 wherein said inserts do not appreciably restrict the contractile motion of tissue adjacent said inserts.

24. The system of claim 1 wherein each of said inserts includes a longitudinal axis and is flexible with respect to said axis.

25. A system for vascularizing a selected portion of the myocardium of the heart of a living being, said system comprising plural elongated inserts for introduction in the selected portion of the myocardium, the selected portion of the myocardium having a plurality of channels formed therein, at least a portion of each of said inserts being formed of a resorbable material, said inserts being arranged for deployment at spaced locations from one another within respective ones of the channels in the selected portion of the myocardium, said inserts being constructed so that when they are deployed within the channels they do not significantly limit the contractility of the being's heart, said inserts being of a size sufficient to substantially fill the channels until resorbed, said resorbable material of said inserts eliciting a foreign body or healing response in the tissue making up the selected portion of the myocardium to enhance to flow of blood therein.

26. The system of claim 25 wherein each of said inserts is arranged to enable blood to flow therethrough.

27. The system of claim 26 wherein each of said inserts is porous.

28. The system of claim 25 wherein said system includes means to limit the depth of penetration of said inserts into the myocardium.

29. The system of claim 25 additionally comprising an instrument for introducing said inserts into the myocardium.

30. The system of claim 29 wherein said instrument is arranged to be inserted into the interior of the heart to introduce said inserts into the myocardium via the endocardium.

31. The system of claim 29 wherein said instrument is arranged to be inserted into the chest cavity to introduce said inserts into the myocardium via the epicardium.

32. The system of claim 29 additionally comprising means for monitoring the cardiac cycle and for coordinating the operation of said deployment means with the cardiac cycle.

33. The system of claim 29 wherein said system includes stabilizing means for stabilizing the position of said instrument adjacent the myocardium during the deployment of said inserts.

34. The system of claim 29 wherein said instrument is arranged to provide one or more of the group consisting of pharmaceuticals, biologically active materials, growth factors, radioactive materials, and radiopaque materials.

35. The system of claim 29 wherein said instrument is arranged to provide one or more of the group consisting of pharmaceuticals, biologically active materials, growth factors, radioactive materials, and radiopaque materials.

36. The system of claim 25 wherein said system includes piercing means for producing the channel in the myocardium.

37. The system of claim 36 wherein said instrument is arranged to deploy said insert into the channels after the formation thereof.

38. The system of claim 36 wherein said piercing means comprises a member arranged to mechanically pierce the myocardium.

39. The system of claim 36 wherein said piercing means comprises means for applying energy to the myocardium to produce the channels.

40. The system of claim 39 wherein said energy is selected from the group comprising one or more of electrical, thermal, electromagnetic, vibratory, hydraulic, pneumatic, and nuclear energy.

41. The system of claim 36 wherein said piercing means comprises means for applying a biologically active material to the myocardium to result in the production of the channels.

42. The system of claim 25 wherein said inserts additionally comprises one or more of the group consisting of pharmaceuticals, biologically active materials, growth factors, radioactive materials, and radiopaque materials.

* * * * *